United States Patent [19]
Coates et al.

[11] Patent Number: 5,549,687
[45] Date of Patent: Aug. 27, 1996

[54] RETROFIT POSTERIOR STABILIZING HOUSING IMPLANT FOR REPLACEMENT KNEE PROSTHESIS

[75] Inventors: Bradley J. Coates; Dominic R. Fosco, both of Cordova, Tenn.

[73] Assignee: Wright Medical Technology, Inc., Arlington, Tenn.

[21] Appl. No.: 285,499

[22] Filed: Aug. 3, 1994

Related U.S. Application Data

[63] Continuation of Ser. No. 988,611, Dec. 10, 1992, abandoned.

[51] Int. Cl.⁶ ........................................ A61F 2/38
[52] U.S. Cl. ................................ 623/20; 606/88
[58] Field of Search ..................... 623/20, 18; 606/88

[56] References Cited

U.S. PATENT DOCUMENTS

| | | |
|---|---|---|
| 4,213,209 | 7/1980 | Insall, et al. . |
| 4,298,992 | 11/1981 | Burstein, et al. . |
| 4,714,474 | 12/1987 | Brooks, Jr. et al. ............... 623/20 |
| 4,721,104 | 1/1988 | Kaufman et al. ............... 606/88 |
| 4,822,366 | 4/1989 | Bolesky ............... 623/20 |
| 4,888,021 | 12/1989 | Forte et al. ............... 623/20 |
| 5,098,436 | 3/1992 | Ferrante, et al. ............... 606/88 |
| 5,100,409 | 3/1992 | Coates et al. ............... 606/88 |
| 5,147,406 | 9/1992 | Houston et al. ............... 623/20 |

FOREIGN PATENT DOCUMENTS

| | | | |
|---|---|---|---|
| 3429157 | 2/1986 | Germany | 623/20 |
| 4102509 | 7/1992 | Germany | 623/20 |

OTHER PUBLICATIONS

Matthews et al., "The Spherocentric Knee", Clinical Orthopedics, 94, Jul.-Aug. 1973, pp. 234-241.

*Primary Examiner*—David H. Willse
*Attorney, Agent, or Firm*—Walker, McKenzie & Walker, P.C.

[57] ABSTRACT

A retrofit posterior stabilizing housing is disposed in a resected receptacle in the trochlear groove of a human femur during revision surgery through the intercondylar notch of a previously implanted condylar-type femoral prosthetic component. The posterior stabilizing housing is dimensioned to pass through the notch in the existing implant and seat superiorly to the trochlear opening of the notch. The posterior stabilizing housing includes medial and lateral side walls extending from a proximal ceiling portion, and anterior and posterior end walls disposed between the side walls, defining a box-like container. An aperture is formed in each of the side walls for receiving screw-like fasteners anchored in the cancellous bone portion of the femur. A pair of anchor posts extend superiorly from the ceiling portion for fixation within the femur. The posterior stabilizing housing may either be cemented in place or the superior surface thereof textured to enhance bone ingrowth.

1 Claim, 3 Drawing Sheets

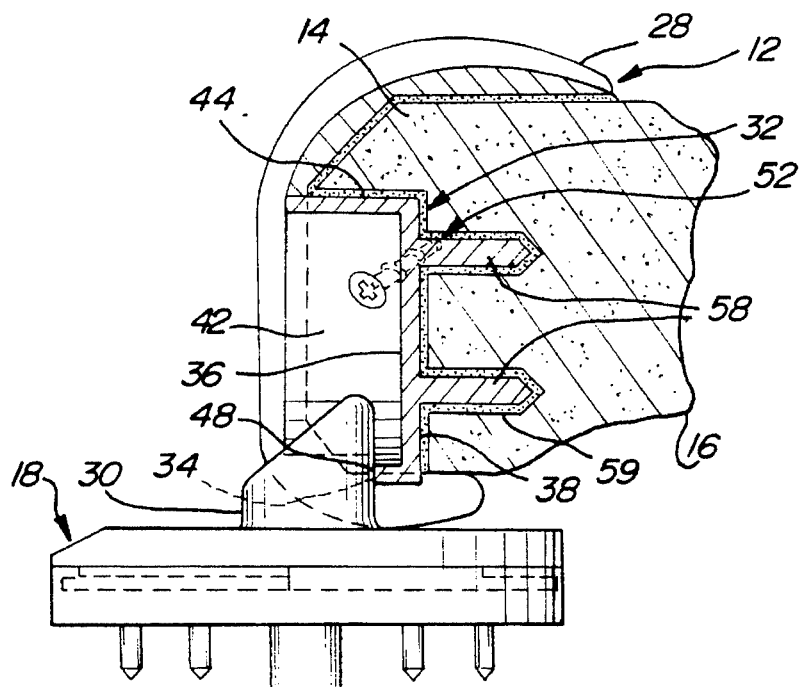
*Fig-3*
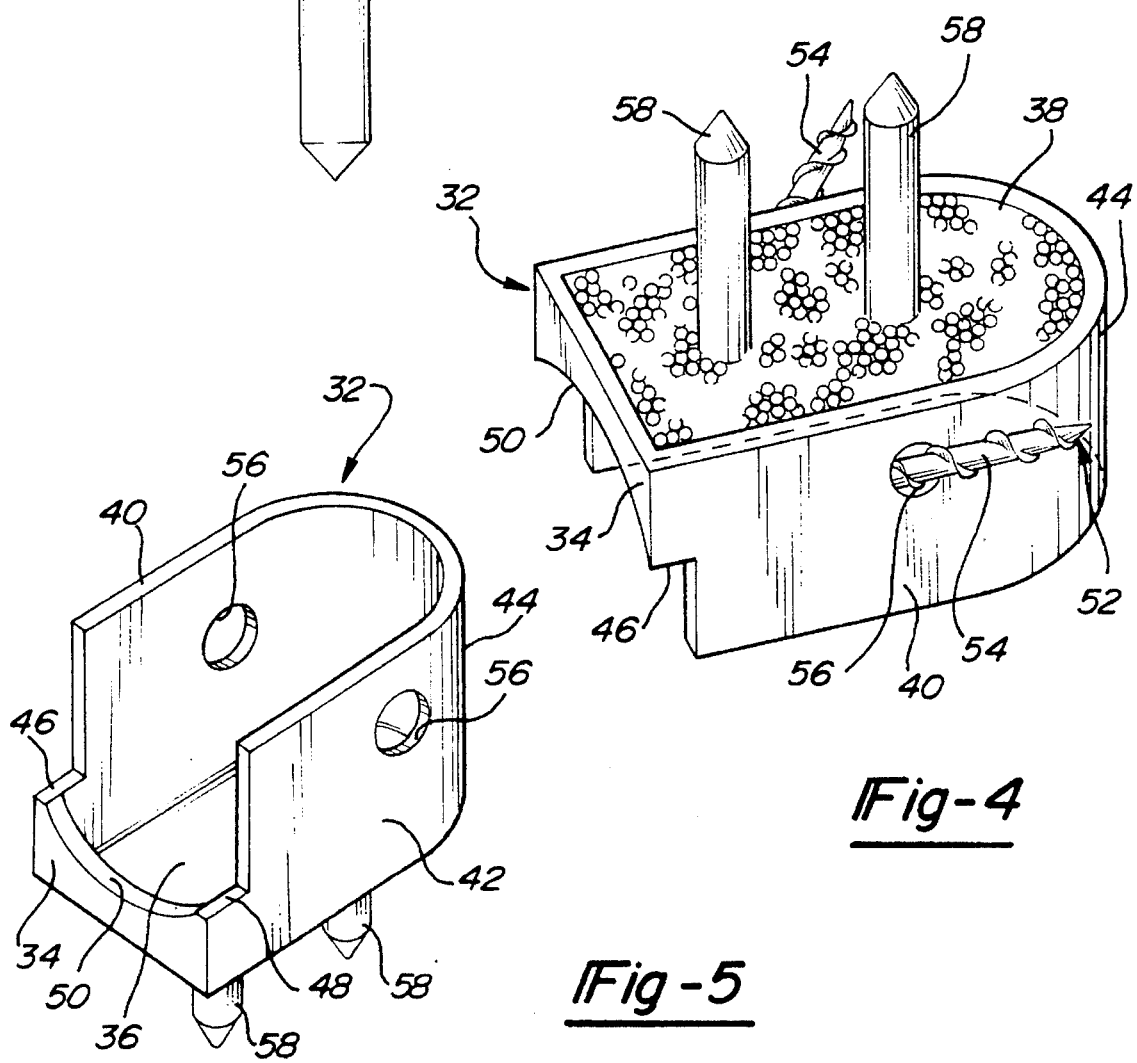
*Fig-4*
*Fig-5*

RETROFIT POSTERIOR STABILIZING HOUSING IMPLANT FOR REPLACEMENT KNEE PROSTHESIS

This application is a continuation of application Ser. No. 07/988,611, filed Dec. 10, 1992, now abandoned.

TECHNICAL FIELD

The invention relates generally to total knee arthroplasty utilizing surgically implantable knee joint prosthetic components. More particularly, the invention relates to revision arthroplasty where converting a condylar type to a posterior-stabilized prosthesis is indicated.

BACKGROUND ART

Knee arthroplasty is becoming more common to partially or totally replace knee joint components which have been damaged due to trauma or disease. Depending upon the condition of the ligaments and tendons surrounding the joint, a surgeon can select a prosthetic component which provides the necessary degree of stability to the total joint. Provided the cruciate ligaments are sufficiently stable, a prosthesis can be selected which utilizes the natural soft tissue structures. This approach is preferred since the complex operation of the knee is most difficult to duplicate artificially.

A posterior-stabilized femoral prosthesis is indicated for a patient suffering from an unstable, painful knee joint where the instability is caused by the lack of or inadequacy of the posterior cruciate ligament. The posterior stabilized knee joint consists of a tibial component having a stabilizing post protruding from the superior surface, or table, of the tibial component, and a femoral component with a stabilizing housing to accept the stabilizing post to provide the stability which the patient's knee joint lacks. Examples of posteriorly stabilized total knee joint prosthesis may be had in U.S. Pat. Nos. 4,213,209 to Insall et al, issued Jul. 22, 1980, and 4,298,992 to Burstein et al, issued Nov. 10, 1981.

According to the prior art, a posterior stabilizing housing typically has been formed as an integral part of the femoral component, such that the receptacle for receiving the posterior stabilizing housing in the bone is formed interoperatively during initial implantation of the femoral component. Formation of such a receptacle for the posterior stabilizing housing is illustrated in U.S. Pat. Nos. 4,721,104 to Kaufman et al, issued Jan. 26, 1988, 5,098,436 to Ferrante et al, issued Mar. 24, 1992, and U.S. Ser. No. 839,425 to Ferrante et al, filed Feb. 20, 1992, and all assigned to the assignee of the subject invention, the entire disclosures of which are hereby expressly incorporated by reference and relied upon.

As mentioned above, if the patient's ligaments are sufficiently stabilized, a conventional condylar-stabilized component is preferably implanted, the ligaments retained intact, thus resulting in a more natural and better functioning prosthesis. Even though satisfactory upon initial implantation surgery, over time the patient's ligaments may deteriorate so they no longer adequately stabilize the artificial knee joint. Under these circumstances, revision surgery is necessary to convert the femoral component and tibial component of the prosthesis to the posterior stabilized type, such as shown in U.S. Pat. No. 4,714,474 to Brooks, Jr. et al, issued Dec. 22, 1987 and assigned to the assignee of the subject invention, the disclosure of which is hereby expressly incorporated by reference and relied upon.

According to the prior art mentioned above, during revision surgery the condylar-stabilized type of femoral component must be removed and replaced by a posterior-stabilized femoral component. It will be readily appreciated that removal of the old femoral component and replacement of the posterior-stabilized type femoral component causes additional and considerable surgical trauma to the bone. Also, the revision surgical procedure requires long anesthetization periods and is a labor-intensive surgical procedure.

It is further understood that removal of the superior articulating tibial table(not shown), made of plastic, can be conventionally done without the necessity for removing the entire implanted portion of the tibial component, in the case where conversion to a posterior-stablized component is indicated, or where the table becomes worn. However, there is still a need to provide this type of modularity with respect to the femoral components since in many revision surgeries, this condylar-stabilized prosthesis is not worn-out and, moreover, good fixture to bones has been achieved.

SUMMARY OF THE INVENTION AND ADVANTAGES

The subject invention provides a modular femoral prosthetic component for implantation upon the distal articular portion of a surgically prepared femur having a trochlear groove and disposed for articulating with a corresponding (complementary) tibial component in total knee arthroplasty. The subject prosthesis comprises a femoral component including a medial condyle, a lateral condyle spaced from the medial condyle, a posteriorly extending trochlear notch disposed between the medial and lateral condyles, and a patella guide interconnecting the medial and lateral condyles extending anteriorly from an intercondylar opening to the trochlear notch. A retrofit posterior stabilizing housing is separate and disjointed from the femoral component and moveable into an operative position in the trochlear notch for engaging an articulating posterior stabilizing post on the tibial component.

A primary advantage of the subject invention is that the prior art condylar stabilized femoral component remains undisturbed on the distal articular surface of the femur, with only a receptacle in the form of a deep recess being resected in the femur to receive the retrofit posterior stabilizing housing. A further advantage of the subject invention is that such limited revision surgery results in reduced surgical trauma to the bone. Another advantage of the subject invention is that, compared to complete femoral component replacement during revision surgery, the retrofit posterior stabilizing housing implantation surgery requires a shorter period of anesthetization during the revision surgery. And yet another advantage is that the retrofit posterior stabilizing housing greatly simplifies the surgical implantation procedures, reducing surgical time.

FIGURES IN THE DRAWINGS

Other advantages of the present invention will be readily appreciated as the same becomes better understood by reference to the following Detailed Description when considered in connection with the accompanying Drawings wherein:

FIG. 3 is a side view as in FIG. 2 showing the femur reflected 90°;

FIG. 4 is a perspective view of the posterior stabilizing housing;

FIG. 5 is an inverted perspective view of the posterior stabilizing housing;

DETAILED DESCRIPTION OF THE PREFERRED EMBODIMENT

Figure 1:
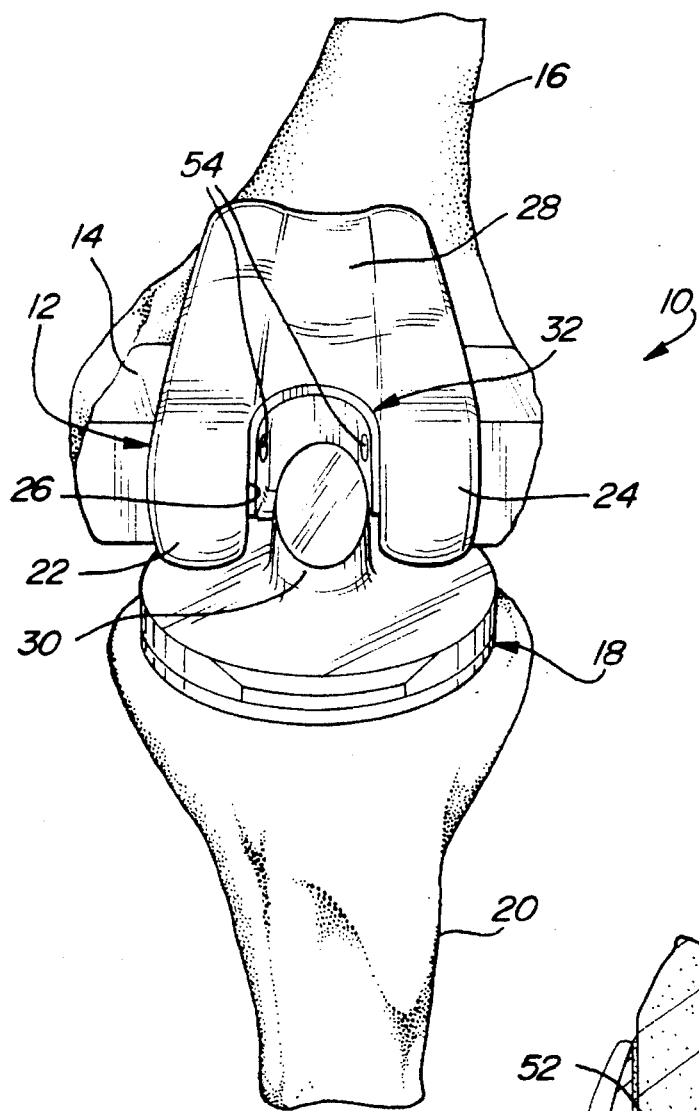
FIG. 1 is a simplified perspective view of the subject femoral prosthesis implanted upon a representative distal femur and disposed for articulation with a corresponding tibial component implanted on a proximal tibia.

Referring to the Figures, wherein like numerals indicate like or corresponding parts throughout the several views, a posterior stabilized total knee replacement prosthesis according to the subject invention is generally shown at 10 in FIG. 1. The prosthesis 10 includes a femoral component, generally indicated at 12, implanted upon the prepared surface of the distal articular portion 14 of a human femur 16. The femoral component 12 is disposed for articulating with a corresponding tibial component, generally shown at 18. The tibial component 18 is shown implanted upon the proximal articular surface of a tibia 20.

The femoral component 12 includes a medial condyle 22 having a predetermined cam-like curvature for approximating the anatomical medial condyle. The femoral component 12 also includes a lateral condyle 24 spaced from the medial condyle 22. The lateral condyle 24 is cam-like in curvature for approximating an anatomical lateral condyle. A post-like stake 25 extends from the superior surfaces of each of the medial 22 and lateral 24 condyles for anchoring the femoral component 12 to the femur 16.

A posteriorly extending trochlear notch 26 is disposed between the medial 22 and lateral 24 condyles. The intercondylar trochlear notch 26 is positioned to approximate a trochlear notch found in anatomical femurs, and in the case of a natural ligament stabilized prosthesis, the trochlear notch 26 articulates on a button or post extending upwardly, or superiorly, from the table of the tibial component 18.

The femoral component 12 further includes a patella guide 28 formed integral with and interconnecting the medial 22 and lateral 24 condyles and extending anteriorly from the trochlear notch 26. The patella guide 28 forms a tongue-like appendage for contacting and guidably supporting either a natural or prosthetic patella (not shown).

Figure 2:
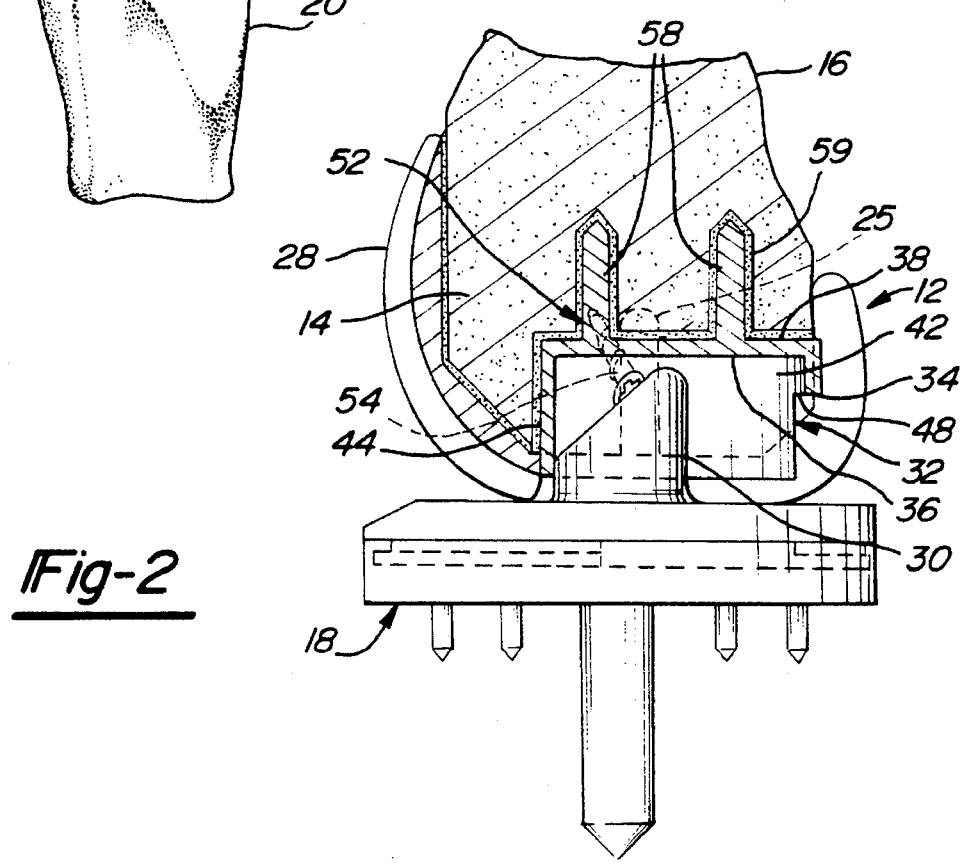
FIG. 2 is a side view of the subject prosthesis showing the femoral component implanted on a sectioned femur.

As discussed supra, a posterior stabilized knee prosthesis is indicated for patients that suffer a lack or inadequacy of the posterior cruciate ligament. The posterior stabilized prosthesis 10 includes a stabilizing post 30 protruding from the superior surface, or table, of the tibial component 18, as shown in FIGS. 1–2. Also, in a posterior stabilized prosthesis 10, the femoral component 12 is provided with a posterior stabilizing housing, generally indicated at 32 in FIGS. 1–6. The posterior stabilizing housing 32 receives the stabilizing post 30 to provide the stability which the patient's natural ligaments lack. The posterior stabilizing housing 32 is moveable into an operative position in the trochlear notch 26, i.e., between the medial 22 and lateral 24 condyles, and embedded within the cancellous bone of the distal femur.

The posterior stabilizing housing 32 includes a posterior end wall 34 which is recessed superiorly with respect to the medial 22 and lateral 24 condyles for engaging the stabilizing post 30 on the tibial component 18. As best shown in FIG. 3, the posterior end wall 34 engages the stabilizing post 30, and thus stabilizes the femoral component 12 relative to the tibial component 18, during reflection of the knee.

Figure 6:
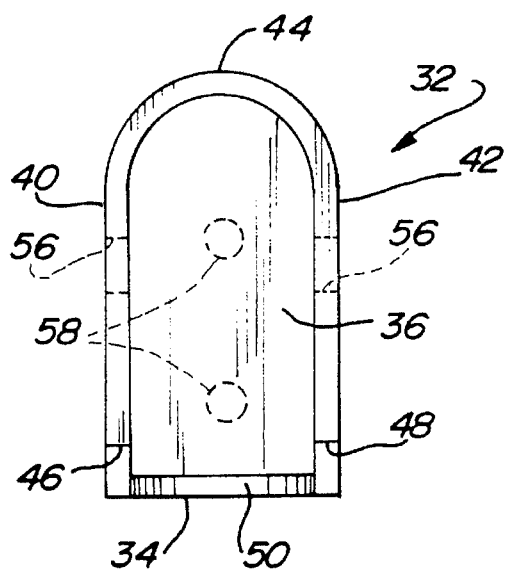
FIG. 6 is a bottom view of the posterior stabilizing housing.

Referring now to FIGS. 2–6, the posterior stabilizing housing 32 is shown including a generally flat ceiling portion 36 extending orthogonally from the posterior end wall 34. As shown in FIG. 4, the ceiling portion 36 has a texture, or porous, superior surface 38 for enhancing adhesion with bone cement or, in the event bone cement is not used, promoting bone ingrowth. The posterior stabilizing housing 32 further includes a pair of side walls 40, 42 extending perpendicularly from the ceiling portion 36 on opposite sides of the posterior end wall 34. The side walls 40, 42 are respectively disposed adjacent the medial 22 and lateral 24 condyles of the femoral component 12. An anterior end wall 44 extends from the ceiling portion 36, spaced from the posterior end wall 34, and interconnects the side walls 40, 42. As illustrated in FIGS. 5 and 6, the anterior end wall 44 is curved to snugly fit adjacent the anterior terminal end of the trochlear notch 26, as shown in FIG. 1. The side walls 40, 42 may include respective notches, or steps 46, 48 adjacent to and flush with the posterior end wall 34. Also, as best shown in FIG. 5, the posterior end wall 34 includes an arcuate engagement surface 50 for better articulating with the stabilizing post 30 of the tibial component 18.

According to the improvement of the subject invention, the posterior stabilizing housing 32 includes fixation means, generally indicated at 52 in FIGS. 1–6, for fixing the posterior stabilizing housing 32 in the operative position in the femur 16 and cooperative with the femoral component 12 to form an integral prosthesis and to permit retrofit implantation of the posterior stabilizing housing 32 in the femoral component 12 during revision surgery. In other words, the posterior stabilizing housing 32 is fabricated separately and independently from the femoral component 12 so that during subsequent revision surgery of the prosthesis 10, the femoral component 12 can be converted from the condylar type to the posterior stabilized type simply by forming an appropriate receptacle in the distal femur 16 and implanting the posterior stabilizing housing 32 through the trochlear notch 26. The fixation means 52 thus provides the mechanism for securing the retrofit posterior stabilizing housing 32 operatively in the prosthesis 10.

Referring now to FIGS. 2–4, the fixation means 52 is shown including at least one, and preferably two, threaded fasteners 54. The threaded fasteners 54 take the form of standard surgical screws driven through the side walls 40, 42 and anchored in the cancellous portion of the bone. Accordingly, an aperture 56 is disposed in each of the side walls 40, 42 for receiving the threaded fasteners 54.

The fixation means 52 also includes at least one, and preferably two, anchor posts 58 extending perpendicularly and superiorly from the superior surface 38 of the ceiling portion 36. The anchor posts 58 include pointed leading ends for permitting the anchor posts 58 to be either forcibly driven into cancellous portion of the bone in a spike-like manner, or cemented in corresponding receptacles drilled in the bone. Alternatively, the leading ends of the anchor posts 58 may be rounded, i.e., hemispherical, to prevent bone splits. As shown in FIG. 4, the anchor post 58 are aligned in anterior-posterior fashion and have a generally cylindrical structure.

Additionally, the fixation means 52 includes standard bone cement 59 applied in the usual manner during the revision surgery to adhesively fasten the entire outer surface of the posterior stabilizing housing 32 to the receptacle formed in the distal femur 16. And, as mentioned above, the anchor posts 58 may be cemented as well.

Figure 7:
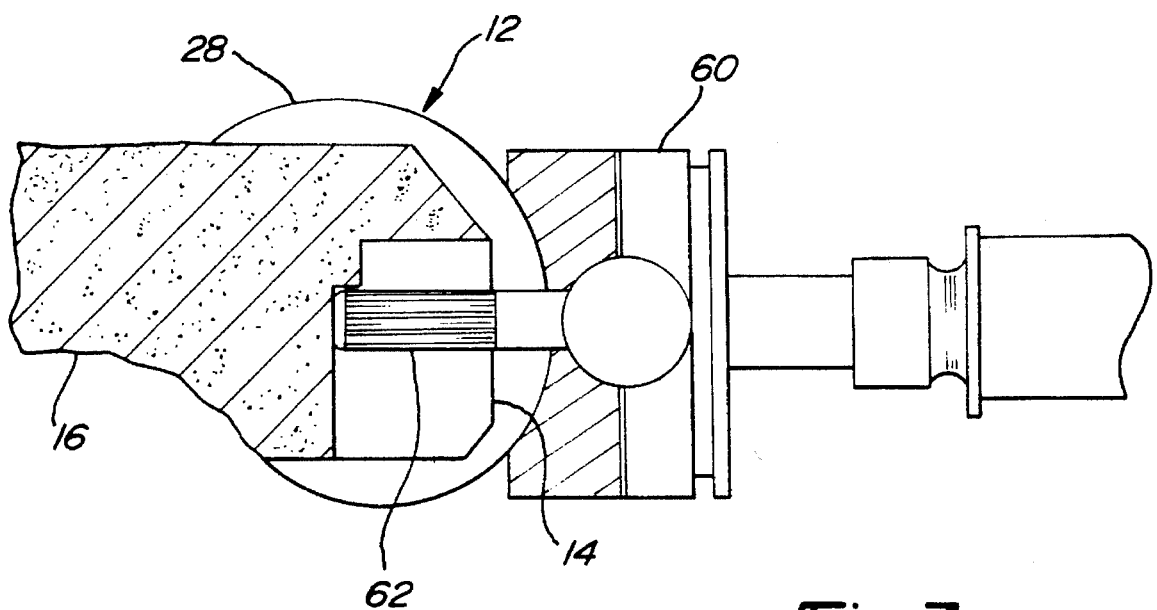
FIG. 7 is a side view of a guide and housing reamer showing a receptacle for the posterior stabilizing housing being formed in a distal femur adjacent an implanted femoral component.

Referring now to FIG. 7, a guide 60 and cooperating housing reamer 62 are shown in simplified, explanary fashion operatively disposed against the femoral component 12. During revision surgery, the housing reamer 62 is advanced into the guide 60 while turning at full speed. The guide 60 is used to direct the angle and position of the housing reamer 62. An oscillating saw (not shown) can be used to remove the posterior aspects of the bone in the recess thus formed. As an alternative, ronguers may be used to remove the posterior bone segments. For a more detailed explanation of an adaptable technique for forming a receptacle or recess in the femur 16 to receive the retrofit posterior stabilizing housing 32, reference is made to U.S. Pat. No. 5,098,436, and U.S. Ser. No. 839,425 both in the name of Ferrante et al, the entire disclosures of which are relied upon.

The subject invention overcomes the disadvantages of the prior art knee joint prostheses in that the functional and well affixed femoral component 12 of a condylar prosthesis remains attached to the femur 16 during revision surgery to convert the prosthesis 10 to a posterior stabilized type prosthesis 10. The posterior stabilizing housing 32 is dimensioned to fit within the trochlear notch 26 of the femoral component 12, between the medial 22 and lateral 24 condyles, with fixation means 52 provided by way of threaded fasteners 54, anchor posts 58, and bone cement 59 so as to independently and separately secure the posterior stabilizing housing 32 within the femur 16. Thus, additional and considerable surgical trauma to the bone is avoided, and further greatly simplifies the revision surgery procedure.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A retrofit posterior stabilizing housing for securing to the distal portion of a surgically prepared femur of a knee joint having a previously implanted femoral component and an implanted complementary tibial component during revision surgery and for articulating with the implanted complementary tibial component; the previously implanted femoral component including a medial condyle and a lateral condyle spaced from the medial condyle with a posteriorly extending trochlear notch disposed between the medial and lateral condyles; the distal portion of the femur having a recess surgically formed therein through the posteriorly extending trochlear notch; the implanted complementary tibial component having a stabilizing post extending through the posterior extending trochlear notch and into the recess in the distal portion of the femur; the recess in the distal portion of the femur having an opened posterior end and an anterior end; the retrofit posterior stabilizing housing comprising:

(a) a body including:
  i. an anterior end wall means for covering at least a portion of the anterior end of the recess in the distal portion of the femur and for engaging the stabilizing post of the implanted complementary tibial component when the retrofit posterior stabilizing housing is secured to the distal portion of the surgically prepared femur and the knee joint is extended to stabilize the knee joint;
  ii. a posterior end wall means for extending across and blocking at least a portion of the opened posterior end of the recess in the distal portion of the femur, and for engaging the stabilizing post of the implanted complementary tibial component when the retrofit posterior stabilizing housing is secured to the distal portion of the surgically prepared femur and the knee joint is flexed to stabilize the knee joint;
  iii. a first side wall means for covering a portion of the recess in the distal portion of the femur;
  iv. a second side wall means for covering a portion of the recess in the distal portion of the femur;
  v. the posterior end wall means, the anterior end wall means, the first side wall means, and the second side wall means are joined to one another with the posterior and anterior end wall means and the first and second side wall means spaced apart from one another to form a receptacle therebetween for receiving the stabilizing post of the implanted complementary tibial component; and (b) means for fixing the body to the distal portion of the femur without requiring removal of the previously implanted femoral component; the means for fixing the body to the distal portion of the femur including bone cement for fixing the body to the distal portion of the femur without requiring removal of the previously implanted femoral component.

* * * * *